United States Patent
Kolberg et al.

(12)

(10) Patent No.: US 6,235,465 B1
(45) Date of Patent: May 22, 2001

(54) HTLV-1 PROBES FOR USE IN SOLUTION PHASE SANDWICH HYBRIDIZATION ASSAYS

(75) Inventors: Janice A. Kolberg, Hercules; Michael S. Urdea, Alamo, both of CA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 08/427,569

(22) Filed: Apr. 24, 1995

Related U.S. Application Data

(63) Continuation of application No. 08/130,150, filed on Sep. 29, 1993, now abandoned, which is a continuation of application No. 07/813,585, filed on Dec. 23, 1991, now abandoned.

(51) Int. Cl.[7] .............................. C12Q 1/70; C12Q 1/68; C12P 19/34
(52) U.S. Cl. ................... 435/5; 435/6; 435/91.2; 536/24.3; 536/24.31; 536/24.33
(58) Field of Search .................... 435/6, 91.2, 5; 536/24.3, 24.31, 24.32

(56) References Cited

U.S. PATENT DOCUMENTS

| | | | |
|---|---|---|---|
| 3,912,805 | * 10/1975 | Cayzer et al. | ................ 436/534 |
| 4,868,105 | 9/1989 | Urdea et al. . | |
| 5,124,246 | 6/1992 | Urdea et al. . | |

FOREIGN PATENT DOCUMENTS

0139489 * 9/1984 (EP) ........................................ 435/6

8903891 * 5/1989 (WO) ........................................ 435/6

OTHER PUBLICATIONS

U.S. Ser. No. 07/813,583, filed Dec. 23, 1991, now abandoned in favor of continuation application U.S. Ser. No. 08/169,715, filed Dec. 17, 1993.

U.S. Ser. No. 07/813,590, filed Dec. 23, 1991, now abandoned in favor of continuation application U.S. Ser. No. 08/138,608, filed Oct. 15, 1993.

U.S. Ser. No. 07/813,586, filed Dec. 23, 1991, now abandoned in favor of continuation application U.S. Ser. No. 08/186,229, filed Jan. 24, 1994.

U.S. Ser. No. 07/813,587, filed Dec. 23, 1991.

U.S. Ser. No. 07/813,589, filed Dec. 23, 1991.

Meytes et al., *Lancet* (1990) 336(8730):1533–1535.

Seiki M., et al. Proc. Natl. Acad. Sci. 80:3618–3622 (1983) (Seq ID #6, Seq ID #42).*

* cited by examiner

Primary Examiner—Jeffrey Fredman
(74) Attorney, Agent, or Firm—Morrison & Foerester LLP

(57) ABSTRACT

Synthetic oligonucleotides which are useful as probes in a solution phase sandwich hybridization assay for the detection of HTLV-1 are described. The oligonucleotides have a first segment comprising a nucleotide sequence substantially complementary to a segment of HTLV-1 nucleic acid, and a second segment comprising a nucleotide sequence which is not complementary to HTLV-1 nucleic acid but is substantially complementary to an oligonucleotide unit of a nucleic acid multimer or to an oligonucleotide bound to a solid phase. Amplified nucleic acid hybridization assays using the probes are exemplified.

20 Claims, No Drawings

HTLV-1 PROBES FOR USE IN SOLUTION PHASE SANDWICH HYBRIDIZATION ASSAYS

This application is a continuation of U.S. Ser. No. 08/130,150 filed Sep. 29, 1993 now abandoned, which is a continuation of U.S. Ser. No. 07/813,585 filed Dec. 23, 1991 now abandoned.

TECHNICAL FIELD

This invention is in the field of nucleic acid hybridization assays. More specifically, it relates to novel nucleic acid probes for detecting HTLV-1.

BACKGROUND ART

HTLV-1 is a human lymphotrophic retrovirus which causes adult T-cell leukemia/lymphoma and tropic spastic paraparesis/HTLV-1-associated myelopathy. These HTLV-1 associated diseases are endemic in Japan and the Caribbean, with sporadic occurrences in the U.S. Detection of HTLV-1 is typically done by immunological or polymerase chain reaction assays (see, e.g., Meytes, et al., *Lancet* 336(8730): 1533–1535, 1990).

Commonly owned U.S. Pat. No. 4,868,105, issued Sep. 19, 1989describes a solution phase nucleic acid sandwich hybridization assay in which analyte nucleic acid is first hybridized in solution to a labeling probe set and to a capturing probe set in a first vessel. The probe-analyte complex is then transferred to a second vessel that contains a solid-phase-immobilized probe that is substantially complementary to a segment of the capturing probes. The segments hybridize to the immobilized probe, thus removing the complex from solution. Having the analyte in the form of an immobilized complex facilitates subsequent separation steps in the assay. Ultimately, single stranded segments of the labeling probe set are hybridized to labeled probes, thus permitting the analyte-containing complex to be detected via a signal generated directly or indirectly from the label.

Commonly owned European Patent Application (EPA) 883096976 discloses a variation in the assay described in U.S. Pat. No. 4,868,105, issued Sep. 19, 1998, in which the signal generated by the labeled probes is amplified. The amplification involves the use of nucleic acid multimers. These multimers are branched polynucleotides that are constructed to have a segment that hybridizes specifically to the analyte nucleic acid or to a nucleic acid (branched or linear) that is bound to the analyte and iterations of a second segment that hybridize specifically to the labeled probe. In the assay employing the multimer, the initial steps of hybridizing the analyte to label or amplifier probe sets and capturing probe sets in a first vessel and transferring the complex to another vessel containing immobilized nucleic acid that will hybridize to a segment of the capturing probes are followed. The multimer is then hybridized to the immobilized complex and the labeled probes in turn hybridized to the second segment iterations on the multimer. Since the multimers provide a large number of sites for label probe attachment, the signal is amplified. Amplifier and capture probe sequences are disclosed for Hepatitis B virus, *Neisseria gonorrhoeae*, penicillin and tetracycline resistance in *N. gonorrhoeae*, and *Chlamydia trachomatis*.

Commonly owned copending application Ser. No. 558, 897, filed Jul. 27, 1990, describes the preparation of large comb-type branched polynucleotide multimers for use in the above-described solution phase assay. The combs provide greater signal enhancement in the assays than the smaller multimers.

DISCLOSURE OF THE INVENTION

One aspect of the invention is a synthetic oligonucleotide useful as an amplifier probe in a sandwich hybridization assay for HTLV-1 nucleic acid comprising a first segment having a nucleotide sequence substantially complementary to a segment of HTLV-1 nucleic acid, and a second segment having a nucleotide sequence substantially complementary to an oligonucleotide acid multimer.

Another aspect of the invention is a synthetic oligonucleotide useful as a capture probe in a sandwich hybridization assay for HTLV-1 nucleic acid comprising a first segment having a nucleotide sequence substantially complementary to a segment of HTLV-1 nucleic acid; and a second segment having a nucleotide sequence substantially complementary to an oligonucleotide bound to a solid phase.

Another aspect of the invention is a solution sandwich hybridization assay for detecting the presence of HTLV-1 nucleic acid in a sample, comprising (a) contacting the sample under hybridizing conditions with an excess of (i) an amplifier probe oligonucleotide comprising a first segment having a nucleotide sequence substantially complementary to a segment of HTLV-1 nucleic acid and a second segment having a nucleotide sequence substantially complementary to an oligonucleotide unit of a nucleic acid multimer and (ii) a capture probe oligonucleotide comprising a first segment having a nucleotide sequence that is substantially complementary to a segment of HTLV-1 nucleic acid and a second segment that is substantially complementary to an oligonucleotide bound to a solid phase;

(b) contacting the product of step (a) under hybridizing conditions with said oligonucleotide bound to the solid phase;

(c) thereafter separating materials not bound to the solid phase;

(d) contacting the product of step (c) under hybridization conditions with the nucleic acid multimer, said. multimer comprising at least one oligonucleotide unit that is substantially complementary to the second segment of the amplifier probe polynucleotide and a multiplicity of second oligonucleotide units that are substantially complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Another aspect of the invention is a kit for the detection of HTLV-1 nucleic acid in a sample comprising in combination (i) a set of amplifier probe oligonucleotides wherein the amplifier probe oligonucleotide comprises a first segment having a nucleotide sequence substantially complementary to a segment of HTLV-1 nucleic acid and a second segment having a nucleotide sequence substantially complementary to an oligonucleotide unit of a nucleic acid multimer;

(ii) a set of capture probe oligonucleotides wherein the capture probe oligonucleotide comprises a first segment having a nucleotide sequence that is substantially complementary to a segment of HTLV-1 nucleic acid and a second segment that is substantially complementary to an oligonucleotide bound to a solid phase;

(iii) a nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide; and (iv) a labeled oligonucleotide.

MODES FOR CARRYING OUT THE INVENTION

Definitions

"Solution phase nucleic acid hybridization assay" intends the assay techniques described and claimed in commonly owned U.S. Pat. No. 4,868,105 and EPA 883096976.

A "modified nucleotide" intends a nucleotide monomer that may be stably incorporated into a polynucleotide and which has an additional functional group. Preferably, the modified nucleotide is a 5'-cytidine in which the $N^4$-position is modified to provide a functional hydroxy group.

An "amplifier multimer" intends a branched polynucleotide that is capable of hybridizing simultaneously directly or indirectly to analyte nucleic acid and to a multiplicity of polynucleotide iterations (i.e., either iterations of another multimer or iterations of a labeled probe). The branching in the multimers is effected through covalent bonds and the multimers are composed of two types of oligonucleotide units that are capable of hybridizing, respectively, to analyte nucleic acid or nucleic acid hybridized to analyte nucleic acid and to a multiplicity of labeled probes. The composition and preparation of such multimers are described in EPA 883096976 and U.S. Ser. No. 558,897 filed Jul. 27, 1990, the disclosures of which are incorporated herein by reference.

The term "amplifier probe" is intended as a branched or linear polynucleotide that is constructed to have a segment that hybridizes specifically to the analyte nucleic acid and iterations of a second segment that hybridize specifically to an amplifier multimer.

The term "capture probe" is intended as an oligonucleotide having a segment substantially complementary to a nucleotide sequence of the target DNA and a segment that is substantially complementary to a nucleotide sequence of a solid-phase-immobilized probe.

"Large" as used herein to describe the comb-type branched polynucleotides of the invention intends a molecule having at least about 15 branch sites and at least about 20 iterations of the labeled probe binding sequence.

"Comb-type" as used herein to describe the structure of the branched polynucleotides of the invention intends a polynucleotide having a linear backbone with a multiplicity of sidechains extending from the backbone.

A "cleavable linker molecule" intends a molecule that may be stably incorporated into a polynucleotide chain and which includes a covalent bond that may be broken or cleaved by chemical treatment or physical treatment such as by irradiation.

All nucleic acid sequences disclosed herein are written in a 5' to 3' direction. Nucleotides are designated according to the nucleotide symbols recommended by the IUPAC-IUB Biochemical Nomenclature Commission. All nucleotide sequences disclosed are intended to include complementary sequences unless otherwise indicated.

Solution Phase Hybridization Assay

The general protocol for the solution phase sandwich hybridizations is as follows. The analyte nucleic acid is placed in a microtiter well with an excess of two single-stranded nucleic acid probe sets: (1) a set of capture probes, each having a first binding sequence substantially complementary to the analyte and a second binding sequence that is substantially complementary to nucleic acid bound to a solid support, for example, the well surface or a bead, and (2) a set of amplifier probes (branched or linear), each having a first binding sequence that is capable of specific binding to the analyte and a second binding sequence that is capable of specific binding to a segment of the multimer. The resulting product is a three component nucleic acid complex of the two probes hybridized to the analyte by their first binding sequences. The second binding sequences of the probes remain as single-stranded segments as they are not complementary to the analyte. This complex hybridizes to the immobilized probe on the solid surface via the second binding sequence of the capture probe. The resulting product comprises the complex bound to the solid surface via the duplex formed by the oligonucleotide bound to the solid surface and the second binding sequence of the capture probe. Unbound materials are then removed from the surface such as by washing.

The amplification multimer is then added to the bound complex under hybridization conditions to permit the multimer to hybridize to the available second binding sequence (s) of the amplifier probe of the complex. The resulting complex is then separated from any unbound multimer by washing. The labeled oligonucleotide is then added under conditions which permit it to hybridize to the substantially complementary oligonucleotide units of the multimer. The resulting immobilized labeled nucleic acid complex is then washed to remove unbound labeled oligonucleotide, and read.

The analyte nucleic acids may be from a variety of sources, e.g., biological fluids or solids, and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence may be present in double-stranded form, the sequence should be denatured. Denaturation can be carried out by various techniques, such as alkali, generally from about 0.05 to 0.2 M hydroxide, formamide, salts., heat, enzymes, or combinations thereof.

The first binding sequences of the capture probe and amplifier probe that are substantially complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

The number of different amplifier and capture probes used influences the sensitivity of the assay, because the more probe sequences used, the greater the signal provided by the assay system. Furthermore, the use of more probe sequences allows the use of more stringent hybridization conditions, thereby reducing the incidence of false positive results. Thus, the number of probes in a set will be at least one capture probe and at least one amplifier probe, more preferably two capture and two amplifier probes, and most preferably 5–100 capture probes and 5–100 amplifier probes.

Oligonucleotide probes for HTLV-1 were designed by aligning the nucleotide sequences of the pol gene of HTLV-1 Japanese and Caribbean isolates and HTLV-2 available from GenBank. Regions of greatest homology between HTLV-1 isolates were chosen for capture probes, while regions of lesser homology were chosen as amplifier probes. Thus, as additional strains or isolates of HTLV-1 are made available, appropriate probes may be designed by aligning the sequence of the new strain or isolate with the nucleotide sequences used to design the probes of the present invention, and choosing regions of greatest homology for use as capture probes, with regions of lesser homology chosen as amplifier probes. The capture probes of the presently preferred configuration form two clusters, with the amplifier probes clustered between the two capture probe clusters. The nucleotide sequences of the presently preferred probe sets are shown in the examples.

The second binding sequences of the capture probe and amplifier probe are selected to be substantially complementary, respectively, to the oligonucleotide bound to the solid surface and to a segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends exact complementarity wherein each base within the binding region corresponds exactly, and "substantially complementary" intends 90% or greater homology.

The labeled oligonucleotide will include a sequence substantially complementary to the repeated oligonucleotide units of the multimer. The labeled oligonucleotide will include one or more molecules ("labels"), which directly or indirectly provide a detectable signal. The labels may be bound to individual members of the substantially complementary sequence or may be present as a terminal member or terminal tail having a plurality of labels. Various means for providing labels bound to the oligonucleotide sequences have been reported in the literature. See, for example, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids. Res.* (1985) 13:2399; Meinkoth and Wahl, *Anal. Biochem.* (1984) 138:267. The labels may be bound either covalently or non-covalently to the substantially complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, α-β-galactosidase, horseradish peroxidase, alkaline phosphatase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to $10^6$:1. Concentrations of each of the probes will generally range from about $10^{-5}$ to $10^{-9}$ M, with sample nucleic acid concentrations varying from $10^{-21}$ to $10^{-12}$ M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 650° C.

The hybridization reactions are usually done in an aqueous medium, particularly a buffered aqueous medium, which may include various additives. Additives which may be employed include low concentrations of detergent (0.01 to 1%), salts, e.g., sodium citrate (0.017 to 0.17 M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

Kits for carrying out amplified nucleic acid hybridization assays according to the invention will comprise in packaged combination the following reagents: the amplifier probe or set of probes; the capture probe or set of probes; the amplifier multimer; and an appropriate labeled oligonucleotide. These reagents will typically be in separate containers in the kit. The kit may also include a denaturation reagent for denaturing the analyte, hybridization buffers, wash solutions, enzyme substrates, negative and positive controls and written instructions for carrying out the assay.

The following examples further illustrate the invention. These examples are not intended to limit the invention in any manner.

EXAMPLES

Example I

Synthesis of Comb-type Branched Polynucleotide

This example illustrates the synthesis of a comb-type branched polynucleotide having 15 branch sites and sidechain extensions having three labeled probe binding sites. This polynucleotide was designed to be used in a solution phase hybridization as described in EPA 883096976.

All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed PHOSTEL™ reagent (DMT—O—CH₂CH₂—(SO₂)—CH₂CH₂—O—P(—N(iPr)₂)(—O—CH₂CH₂CN) wherein DMT is dimethoxytrityl and iPr is isopropyl) (ABN). Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

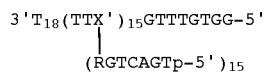

wherein X' is a branching monomer, and R is a periodate cleavable linker.

The portion of the comb body through the 15 (TTX') repeats is first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

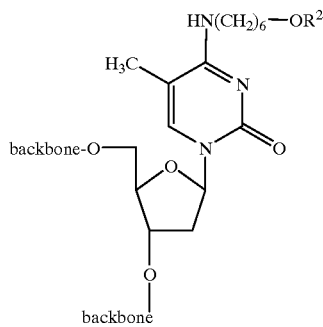

where R² represents

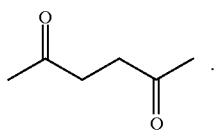

For synthesis of the comb body (not including sidechains), the concentration of beta cyanoethylphosphoramidite monomers was 0.1 M for A, C, G and T, 0.15 M for the branching site monomer E, and 0.2 M for PHOSTEL™ reagent (DMT—O—CH²CH₂—(SO₂)—CH₂CH₂—O—P(—N(iPr)₂)(—O—CH₂CH₂CN) wherein DMT is dimethoxytrityl and iPr is isopropyl). Detritylation was done with 3% trichloroacetic acid in methylene chloride using stepped flowthrough for the duration of the deprotection. At the conclusion the 5' DMT was replaced with an acetyl group.

Cleavable linker R and six base sidechain extensions of the formula 3'-RGTCAGTp (SEQ ID NO:1) were synthesized at each branching monomer site as follows. The base protecting group removal (R² in the formula above) was performed manually while retaining the CPG support in the same column used for synthesizing the comb body. In the case of R²=levulinyl, a solution of 0.5 M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the cleavable linker R and six base sidechain extensions were added using a 6.4 cycle.

In these syntheses the concentration of phosphoramidites was 0.1 M (except 0.2 M R and PHOSTEL™ reagent (DMT—O—CH₂CH₂—(SO₂)—CH₂CH₂—O—P(—N(iPr)₂)(—O—CH₂CH₂CN) wherein DMT is dimethoxytrityl and iPr is isopropyl); R was 2-(4-(4-(2-Dimethoxytrityloxy)ethyl-)phenoxy 2,3-di(benzoyloxy)-butyloxy)phenyl)ethyl-2-cyanoethyl-N,N-diisopropylphosphoramidite).

Detritylation is effected with a solution of 3% trichloroacetic acid in methylene chloride using continuous flowthrough, followed by a rinse solution of toluene/chloromethane (1:1 v/v). Branched polynucleotide chains were removed from the solid supports automatically in the 380B using the cycle "CE NH₃." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 μl water.

3' backbone extensions (segment A), sidechain extensions and ligation template/linkers of the following structures were also made using the automatic synthesizer:

3' Backbone extension

3'-TCCGTATCCTGGGCACAGAGGTGCp-5' (SEQ ID NO:2)

Sidechain extension

3'-GATGCG(TTCATGCTGTTGGTGTAG)₃-5' (SEQ ID NO:3)

Ligation template for linking 3' backbone extension

3'-AAAAAAAAAAGCACCTp-5' (SEQ ID NO:4)

Ligation tem-plate for linking sidechain extension

3'-CGCATCACTGAC-5' (SEQ ID NO:5)

The crude comb body was purified by a standard polyacrylamide gel (7% with 7 M urea and 1×TBE running buffer) method.

The 3' backbone extension and the sidechain extensions were ligated to the comb body as follows. The comb body (4 pmole/μl), 3' backbone extension (6.25 pmole/μl), sidechain extension (93.75 pmole/μl), sidechain linking template (75 pmoles/μl) and backbone linking template (5 pmole/μl) were combined in 1 mM ATP/ 5 mM DTT/50 mM Tris-HCl, pH 8.0/10 mM MgCl₂/2 mM spermidine, with 0.5 units/μl T4 polynucleotide kinase. The mixture was incubated at 37° C. for 2 hr, then heated in a water bath to 95° C., and then slowly cooled to below 35° C. over a 1 hr period. 2 mM ATP, 10 mM DTT, 14% polyethylene glycol, and 0.21 units/μl T4 ligase were added, and the mixture incubated for 16–24 hr at 23° C. The DNA was precipitated in NaCl/ethanol, resuspended in water, and subjected to a second ligation as follows. The mixture was adjusted to 1 mM ATP, 5 mM DTT, 14% polyethylene glycol, 50 mM Tris-HCl, pH 7.5, 10 mM MgCl₂, 2 mM spermidine, 0.5 units/μl T4 polynucleotide kinase, and 0.21 units/μl T4 ligase were added, and the mixture incubated at 23° C. for 16–24 hr. Ligation products were then purified by polyacrylamide gel electrophoresis.

After ligation and purification, a portion of the product was labeled with ³²P and subjected to cleavage at the site of R achieved by oxidation with aqueous NaIo₄ for 1 hr. The sample was then analyzed by PAGE to determine the number of sidechain extensions incorporated by quantitating the radioactive label in the bands on the gel. The product was found to have a total of 45 labeled probe binding sites.

Example II

Procedure for HTLV-1 Assay

A "15×3" amplified solution phase nucleic acid sandwich hybridization assay format is used in this assay. The "15×3" designation derives from the fact that the format employs two multimers: (1) an amplifier probe having a first segment (A) that binds to HTLV-1 and a second segment (B) that hybridizes to (2) an amplifier multimer having a first segment (B*) that hybridizes to the segment (B) and fifteen iterations of a segment (C), wherein segment C hybridizes to three labeled oligonucleotides.

The amplifier and capture probe segments and their respective names used in this assay are as follows.

HTLV-1 Amplifier Probes

HTLV.7 (SEQ ID NO:6) GGTCTGGGTGT-CAAYCTGGGCTTTAATTACGGG
HTLV.8 (SEQ ID NO:7) ATCTAGTARAGCTTCGAT-AGTCTTTGGGTGGCT
HTLV.9 (SEQ ID NO:8) GGCTATCGGAAGGACTGT-CATGTCTGCTCCTGT
HTLV.10 (SEQ ID NO:9) TGTRTTTTTGAGGGGAGTAT-TACTTGAGAACAA
HTLV.11 (SEQ ID NO:10) ATCTTGGGTTTGGCCCCCT-GCCCCTAAYACGGA
HTLV.12 (SEQ ID NO:11) TATTAGCACAGGAAGG-GAGGTGAGCTTAAAGTG
HTLV.13 (SEQ ID NO:12) TAAAACAATAGGCGTYGTC-CGGAAAGGGAGGCG
HTLV.14 (SEQ ID NO:13) CYAGTTGTTTTTGGTAT-CAACTAGGCAAGATGT
HTLV.15 (SEQ ID NO:14) GCATTGTTGTAAGGCAT-CRCGACCTATGATGGC
HTLV.16 (SEQ ID NO:15) CCYTTTTGCCTCAGGGAG-GTACAGGACGCCYTG
HTLV.17 (SEQ ID NO:16) RGCTGGCGCCTGTATTG-GCAAGATTACAGGCGG
HTLV.18 (SEQ ID NO:17) GGGGGGCCTTGGGAGGT-GTTCTAGYCCAAGGAC
HTLV.19 (SEQ ID NO:18) GGCGTTCTGGTTTAAAGG-GAACTGGCTGATTTS
HTLV.20 (SEQ ID NO:19) GGGCCTTCCGGACCAAGT-GTTGCAAGGCCTGGA
HTLV.21 (SEQ ID NO:20) GCCCGGTGTAGGRTTC-GATATGGCCTGCCTCCA
HTLV.22 (SEQ ID NO:21) CYTTTTTAACTGG-GAATACTGGGTTATTYCCTG
HTLV.23 (SEQ ID NO:22) GCAGGTCGTGGAT-GAATCGCCAGGTTCCATTGG
HTLV.24 (SEQ ID NO:23) ATGAGAGRTCTATGGTTA-GAGAGTTAGTGGCCC
HTLV.25 (SEQ ID NO:24) GGCTGGACAAGT-CAGGGGGCCCGGGGAAGATG
HTLV.26 (SEQ ID NO:25) CTAT-AGTTTGYAAGTGGGCTAGTGTRGTTGGCA
HTLV.27 (SEQ ID NO:26) GTARGGGGATTTG-GAAAAAGGCGTCTYTAAGGT
HTLV.28 (SEQ ID NO:27) CAGTGAAAGCAAAG-TAGGGCTGGAACTGTTTAG
HTLV.29 (SEQ ID NO:28) TAGTGCCGGGGCCGTAGT-TACACTGCTGTGGGA
HTLV.30 (SEQ ID NO:29) TAAACCCTTGGGGTAGTAC-TYTCCAGGCGTATC
HTLV.31 (SEQ ID NO:30) CCAGCTGCATTTCGAA-CAGGGTGGGACTATTTT
HTLV,.32 (SEQ ID NO:31) GGAARGCTTGC-CGAATGGGCTGCAGGATATGGG
HTLV.33 (SEQ ID NO:32) TGTCATCCATGTACTGAA-GAATAGTGCATTGGG
HTLV.34 (SEQ ID NO:33) GYAGGTCCKCATGG-GAGGGGCTTGCYAGGAGAA
HTLV.35 (SEQ ID NO:34) TTAGGGAAGCCATTGTGGC-CTCTGAGAGTAGTW
HTLV.36 (SEQ ID NO:35) TTTTGTTTTCGGACACAG-GCAACCCATGGGAGA
HTLV.37 (SEQ ID NO:36) CTAGGAACTTAATTGTTC-CAGGGGTTTGCTGGG
HTLV.38 (SEQ ID NO:37) CATAAGTGAGGTGATTRG-GTGAAATTATYTGCC
HTLV.39 (SEQ ID NO:38) AGCGGGACCGTATAGGTAC-CKTGGGGACTGCAT
HTLV.40 (SEQ ID NO:39) CGCCAAGTAGGGCT-TGAAGTTCAGGTAGCGCCC
HTLV.41 (SEQ ID NO:40) AGGTAGGAGTTCCTTTG-GAGACCCACTGAATCT
HTLV.42 (SEQ ID NO:41) AGGCACAGTAGAGACTGT-GAAGGGGCTGGCGTA

HTLV-1 Capture Probes

HTLV.1 (SEQ ID NO:42) TCTGGTTCTGGGAT-AGTGGGCTTTAGGCGGGGG
HTLV.2 (SEQ ID NO:43) GGGAGRTCTAATAG-GAGGGCATCYTCCTCTGGC
HTLV.3 (SEQ ID NO:44) CCTATGRAGTTTTTTGGGT-GTGGRATGTCRGCG
HTLV.4 (SEQ ID NO:45) CTGTAATGTGGGGGGGGAG-GTTAAACCTCCCCC
HTLV.5 (SEQ ID NO:46) AATAGATGYTGGGTCTTGGT-TARGAARGACTTG
HTLV.6 (SEQ ID NO:47) CCGACGGGCGG-GATCTAACGGTATAACTGGCAG
HTLV.43 (SEQ ID NO:48) ATATTTGGTCTCGGGGAT-CAGTATGCCTTTGTA
HTLV.44 (SEQ ID NO:49) GCACTAATGATTGAACT-TGAGAAGGATTTAAAT
HTLV.45 (SEQ ID NO:50) TGCGGCAGTTCTGTGA-CAGGGCCTGCCGCAGCT
HTLV.46 (SEQ ID NO:51) CCCCTAG-GAGGGGCAGGGTTTGGACTAGTCTAC
HTLV.47 (SEQ ID NO:52) CAGTRGTGGTGCCAGT-GAGGGTCAGCATAATAG
HTLV.48 (SEQ ID NO:53) CAAGTGGCCACTGCTSCT-TGGACTGGAACACYA

Each amplifier probe contains, in addition to the sequences substantially complementary to the HTLV-1 sequences, the following 5' extension complementary to a segment of the amplifier multimer,

AGGCATAGGACCCGTGTCTT (SEQ ID NO:54).

Each capture probe contains, in addition to the sequences substantially complementary to HTLV-1 DNA, the following downstream sequence complementary to DNA bound to the solid phase (XT1*),

CTTCTTTGGAGAAAGTGGTG (SEQ ID NO:55).

Microtiter plates were prepared as follows. White Microlite 1 Removawell strips (polystyrene microtiter plates, 96 wells/plate) were purchased from Dynatech Inc. Each well was filled with 200 µl 1 N HCl and incubated at room temperature for 15–20 min. The plates were then washed 4 times with 1×PBS and the wells aspirated to remove liquid. The wells were then filled with 200 µl 1 N NaOH and incubated at room temperature for 15–20 min. The plates were again washed 4 times with 1×PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1× PBS to a final concentration of 0.1 mg/ml (pH 6.0). 100 µL of this solution was added to each well. The plate was wrapped in plastic to prevent drying and incubated at 30° C. overnight. The plate was then washed 4 times with 1×PBS and the wells aspirated to remove liquid.

The following procedure was used to couple the oligonucleotide XT1* to the plates. Synthesis of XT1* was described in EPA 883096976. 20 mg disuccinimidyl suberate was dissolved in 300 µl dimethyl formamide (DMF). 26 $OD_{260}$ units of XT1* was added to 100 µl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 mM sodium phosphate, pH 6.5, at 4° C. The mixture was vortexed to mix and loaded onto the equilibrated NAP-25 column. DSS-activated XT1* DNA was eluted from the column with 3.5 ml 10 mM sodium phosphate, pH 6.5. 5.6 $OD_{260}$ units of eluted DSS-activated XT1* DNA was added to 1500 ml 50 mM sodium phosphate, pH 7.8. 50 µl of this solution was added to each well and the plates were incubated overnight. The plate was then washed 4 times with 1×PBS and the wells aspirated to remove liquid.

Final stripping of plates was accomplished as follows. 200 µL of 0.2N NaOH containing 0.5% (w/v) SDS was added to each well. The plate was wrapped in plastic and incubated at 65° C. for 60 min. The plate was then washed 4 times with 1×PBS and the wells aspirated to remove liquid. The stripped plate was stored with desiccant beads at 2–8° C.

Test samples were prepared as follows. 1×$10^6$ HTLV-1-infected MT-2 cells or uninfected HuT cells (Human T cell lymphoma cells) were used directly in the assay below or were extracted with a standard phenol:chloroform extraction procedure (See, for example, Sambrook, et al., *Molecular Cloning: A Laboratory Manual,* 1989, Cold Spring Harbor Press, Cold Spring Harbor, N.Y.). Negative controls were Dulbecco's Modified Eagle's Medium (DMEM), negative human serum (neg. HS), buffer (10 mM Tris-HCl, pH 8.0), and distilled $H_2O$. 60 µl P-K Buffer (2 mg/ml proteinase K in 10 mM Tris-HCl, pH 8.0/0.15 M NaCl/10 mM EDTA, pH 8.0/1% SDS/40 µg/ml sonicated salmon sperm DNA) was added to a microfuge tube for each sample to be assayed. 50 µl of test sample was added to each tube.

A cocktail of the HTLV-1-specific amplifier and capture probes listed above was added to each well (10 fmoles of each probe/tube in 25 µl, diluted in 1 N NaOH). The tubes were incubated at 65° C. for 30 min.

65 µl neutralization buffer was then added to each tube (0.77 M 3-(N-morpholino)propane sulfonic acid/1.845 M NaCl/0.185 M sodium citrate). After mixing, the tubes were incubated at 65° C. overnight. Condensation was centrifuged off the walls of each tube and the contents of the tubes transferred to microtiter wells prepared as above. The microtiter plates were incubated at 65° C. for 4 hr.

After an additional 10 min at room temperature, the contents of each well are aspirated to remove all fluid, and the wells washed 2× with washing buffer (0.1% SDS/0.015 M NaCl/0.0015 M sodium citrate).

The amplifier multimer is then added to each well (20 fmoles in 50 µl in 50% horse serum/(0.06 M NaCl/0.06 M sodium citrate/0.1% SDS mixed 1:1 with 4×SSC/0.1% SDS/0.5% "blocking reagent" a purified fraction of dry milk powder, Boehringer Mannheim catalog No. 1096 176). After covering plates and agitating to mix the contents in the wells, the plates are incubated for 30 min at 55° C. After a further 5 min period at room temperature, the wells are washed as described above.

Alkaline phosphatase label probe, disclosed in EP 883096976, is then added to each well (20 fmoles in 50 µl/well). After incubation at 55° C. for 15 min, and 5 min at room temperature, the wells are washed twice as above and then 3× with 0.015 M NaCl/0.0015 N sodium citrate.

An enzyme-triggered dioxetane (Schaap et al., Tet. Lett. (1987) 28:1159–1162 and EPA Pub. No. 0254051), obtained from Lumigen, Inc., was employed. 50 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates are then read on a Dynatech ML 1000 luminometer. Output is given as the full integral of the light produced during the reaction.

Results are shown in the Table below. These results indicate the ability to detect HTLV-1 DNA in both extracted and unextracted infected cells, and no cross-hybridization with components of the uninfected controls.

TABLE

| Sample | # Cells | Sample Prep | Luminometer Reading |
|---|---|---|---|
| MT-2 | $10^6$ | extracted | 48.68 |
| HuT 78 | $10^6$ | extracted | 1.91 |
| MT-2 | $10^6$ | unextracted | 27.39 |
| HuT-78 | $10^6$ | unextracted | 2.37 |
| DMEM | 0 | unextracted | 1.75 |
| Neg. HS | 0 | unextracted | 1.07 |
| Tris | 0 | unextracted | 1.39 |
| $H_2O$ | 0 | unextracted | 1.02 |

Example 3

Detection of HTLV-1 RNA

HTLV-1 RNA is detected using essentially the same procedure as above with the following modifications.

A standard curve of HTLV-1 RNA is prepared by serially diluting HTLV-1 virus stock in normal human serum to a range between 125 to 5000 TCID50/ml. A proteinase K solution is prepared by adding 10 mg proteinase K to 5 ml HTLV-1 capture diluent (53 mM Tris-HCl, pH 8/10.6 mM EDTA/1.3% SDS/16 µg/ml sonicated salmon sperm DNA/ 5.3×SSC/1 mg/ml proteinase K) made 7% in formamide stored at −20° C. Equimolar mixtures of capture probes and label probes are added to the proteinase K solution such that the final concentration of each probe was 1670 fmoles/ml. After addition of 30 µl of the probe/proteinase K solution to each well of microtiter plates prepared as above, 10 µl of appropriate virus dilutions are added to each well. Plates are covered, shaken to mix and then incubated at 65° C. for 16 hr.

Plates are removed from the incubator and cooled on the bench top for 10 min. The wells are washed 2× as described in Example 2 above. The 15×3 multimer is diluted to 1 fmole/µl in Amp/Label diluent (prepared by mixing 2.22 ml DEPC-treated H$_2$O (DEPC is diethylpyrocarbonate), 1.35 ml 10% SDS, 240 µl 1 M Tris pH 8.0, 20 µl horse serum, adjusted to 2 mg/ml in proteinase K and heated to 65° C. for 2 hr, then added to 240 µl of 0.1 M PMSF and heated at 37° C. for 1 hr, after which is added 4 ml DEPC-H$_2$O, 4 ml 10% SDS and 8 ml 20×SSC). The diluted 15×3 multimer is added at 40 µl/well, the plates sealed, shaken, and incubated at 55° C. for 30 min.

The plates are then cooled at room temperature for 10 minutes, and washed as described above. Alkaline phosphatase label probe is diluted to 2.5 fmoles/µl in Amp/Label diluent and 40 µl added to each well. Plates are covered, shaken, and incubated at 55° C. for 15 min.

Plates are cooled 10 min at room temperature, washed 2× as above and then 3× with 0.15 M NaCl/0.015 M sodium citrate. Substrate is added and luminescence measured as above.

Modifications of the above-described modes for carrying out the invention that are obvious to those of skill in biochemistry, nucleic acid hybridization, and related fields are intended to be within the scope of the following claims.

SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
      (A) LENGTH: 7 base pairs
      (B) TYPE: nucleic acid
      (C) STRANDEDNESS: single
      (D) TOPOLOGY: linear (xi) SEQUENCE DESCRIPTION: SEQ ID NO: 1:

TGACTGR                                                                       7

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO: 2:

CGTGGAGACA CGGGTCCTAT GCCT                            24

(2) INFORMATION FOR SEQ ID NO: 3:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO: 3:

GATGTGGTTG TCGTACTTGA TGTGGTTGTC GTACTTGATG TGGTTGTCGT ACTTGCGTAG     60

(2) INFORMATION FOR SEQ ID NO: 4:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO: 4:

TCCACGAAAA AAAAAA                                              16

(2) INFORMATION FOR SEQ ID NO: 5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 5:

CAGTCACTAC GC                                                                12

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 6:

GGTCTGGGTG TCAAYCTGGG CTTTAATTAC GGG                                         33

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 7:

ATCTAGTARA GCTTCGATAG TCTTTGGGTG GCT                                         33

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 8:

GGCTATCGGA AGGACTGTCA TGTCTGCTCC TGT                                         33

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 9:

TGTRTTTTTG AGGGGAGTAT TACTTGAGAA CAA                                         33

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 10:

ATCTTGGGTT TGGCCCCCTG CCCCTAAYAC GGA                                         33

(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 11:

TATTAGCACA GGAAGGGAGG TGAGCTTAAA GTG        33

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 12:

TAAAACAATA GGCGTYGTCC GGAAAGGGAG GCG        33

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 13:

CYAGTTGTTT TTGGTATCAA CTAGGCAAGA TGT        33

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 14:

GCATTGTTGT AAGGCATCRC GACCTATGAT GGC        33

(2) INFORMATION FOR SEQ ID NO: 15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 15:

CCYTTTTGCC TCAGGGAGGT ACAGGACGCC YTG        33

(2) INFORMATION FOR SEQ ID NO: 16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 16:

RGCTGGCGCC TGTATTGGCA AGATTACAGG CGG        33

(2) INFORMATION FOR SEQ ID NO: 17:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 17:

GGGGGGCCTT GGGAGGTGTT CTAGYCCAAG GAC                                            33

(2) INFORMATION FOR SEQ ID NO: 18:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 18:

GGCGTTCTGG TTTAAAGGGA ACTGGCTGAT TTS                                            33

(2) INFORMATION FOR SEQ ID NO: 19:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 19:

GGGCCTTCCG GACCAAGTGT TGCAAGGCCT GGA                                            33

(2) INFORMATION FOR SEQ ID NO: 20:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 20:

GCCCGGTGTA GGRTTCGATA TGGCCTGCCT CCA                                            33

(2) INFORMATION FOR SEQ ID NO: 21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 21:

CYTTTTTAAC TGGGAATACT GGGTTATTYC CTG                                            33

(2) INFORMATION FOR SEQ ID NO: 22:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 22:

GCAGGTCGTG GATGAATCGC CAGGTTCCAT TGG                                            33

(2) INFORMATION FOR SEQ ID NO: 23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 23:

ATGAGAGRTC TATGGTTAGA GAGTTAGTGG CCC                                33

(2) INFORMATION FOR SEQ ID NO: 24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 24:

GGCTGGACAA GTCAGGGGGC CCGGGGGAAG ATG                                33

(2) INFORMATION FOR SEQ ID NO: 25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 25:

CTATAGTTTG YAAGTGGGCT AGTGTRGTTG GCA                                33

(2) INFORMATION FOR SEQ ID NO: 26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 26:

GTARGGGGAT TTGGAAAAAG GCGTCTYTAA GGT                                33

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 27:

CAGTGAAAGC AAAGTAGGGC TGGAACTGTT TAG                                33

(2) INFORMATION FOR SEQ ID NO: 28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 28:

TAGTGCCGGG GCCGTAGTTA CACTGCTGTG GGA                                33

(2) INFORMATION FOR SEQ ID NO: 29:

(i) SEQUENCE CHARACTERISTICS:

(A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 29:

TAAACCCTTG GGGTAGTACT YTCCAGGCGT ATC                               33

(2) INFORMATION FOR SEQ ID NO: 30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 30:

CCAGCTGCAT TTCGAACAGG GTGGGACTAT TTT                               33

(2) INFORMATION FOR SEQ ID NO: 31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 31:

GGAARGCTTG CCGAATGGGC TGCAGGATAT GGG                               33

(2) INFORMATION FOR SEQ ID NO: 32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 32:

TGTCATCCAT GTACTGAAGA ATAGTGCATT GGG                               33

(2) INFORMATION FOR SEQ ID NO: 33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 33:

GYAGGTCCKC ATGGGAGGGG CTTGCYAGGA GAA                               33

(2) INFORMATION FOR SEQ ID NO: 34:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 34:

TTAGGGAAGC CATTGTGGCC TCTGAGAGTA GTW                               33

(2) INFORMATION FOR SEQ ID NO: 35:

(i) SEQUENCE CHARACTERISTICS:
        (A) LENGTH: 33 base pairs (B) TYPE: nucleic acid
            (C) STRANDEDNESS: single
            (D) TOPOLOGY: linear (xi) SEQUENCE DESCRIPTION: SEQ ID NO: 35:

TTTTGTTTTC GGACACAGGC AACCCATGGG AGA                                33

(2) INFORMATION FOR SEQ ID NO: 36:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 36:

CTAGGAACTT AATTGTTCCA GGGGTTTGCT GGG                                33

(2) INFORMATION FOR SEQ ID NO: 37:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 37:

CATAAGTGAG GTGATTRGGT GAAATTATYT GCC                                33

(2) INFORMATION FOR SEQ ID NO: 38:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 38:

AGCGGGACCG TATAGGTACC KTGGGGACTG CAT                                33

(2) INFORMATION FOR SEQ ID NO: 39:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 39:

CGCCAAGTAG GGCTTGAAGT TCAGGTAGCG CCC                                33

(2) INFORMATION FOR SEQ ID NO: 40:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 40:

AGGTAGGAGT TCCTTTGGAG ACCCACTGAA TCT                                33

(2) INFORMATION FOR SEQ ID NO: 41:

(i) SEQUENCE CHARACTERISTICS:
            (A) LENGTH: 33 base pairs
            (B) TYPE: nucleic acid (C) STRANDEDNESS: single
        (D) TOPOLOGY: linear (xi) SEQUENCE DESCRIPTION: SEQ ID NO: 41:

AGGCACAGTA GAGACTGTGA AGGGGCTGGC GTA                              33

(2) INFORMATION FOR SEQ ID NO: 42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 42:

TCTGGTTCTG GGATAGTGGG CTTTAGGCGG GGG                              33

(2) INFORMATION FOR SEQ ID NO: 43:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 43:

GGGAGRTCTA ATAGGAGGGC ATCYTCCTCT GGC                              33

(2) INFORMATION FOR SEQ ID NO: 44:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 44:

CCTATGRAGT TTTTTGGGTG TGGRATGTCR GCG                              33

(2) INFORMATION FOR SEQ ID NO: 45:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 45:

CTGTAATGTG GGGGGGAGG TTAAACCTCC CCC                               33

(2) INFORMATION FOR SEQ ID NO: 46:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 46:

AATAGATGYT GGGTCTTGGT TARGAARGAC TTG                              33

(2) INFORMATION FOR SEQ ID NO: 47:

(i) SEQUENCE CHARACTERISTICS:
        (A) LENGTH: 33 base pairs
        (B) TYPE: nucleic acid
        (C) STRANDEDNESS: single (D) TOPOLOGY: linear (xi) SEQUENCE DESCRIPTION: SEQ ID NO: 47:

CCGACGGGCG GGATCTAACG GTATAACTGG CAG                33

(2) INFORMATION FOR SEQ ID NO: 48:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 48:

ATATTTGGTC TCGGGGATCA GTATGCCTTT GTA                33

(2) INFORMATION FOR SEQ ID NO: 49:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 49:

GCACTAATGA TTGAACTTGA GAAGGATTTA AAT                33

(2) INFORMATION FOR SEQ ID NO: 50:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 50:

TGCGGCAGTT CTGTGACAGG GCCTGCCGCA GCT                33

(2) INFORMATION FOR SEQ ID NO: 51:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 51:

CCCCTAGGAG GGGCAGGGTT TGGACTAGTC TAC                33

(2) INFORMATION FOR SEQ ID NO: 52:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 52:

CAGTRGTGGT GCCAGTGAGG GTCAGCATAA TAG                33

(2) INFORMATION FOR SEQ ID NO: 53:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 53:

CAAGTGGCCA CTGCTSCTTG GACTGGAACA CYA                33

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 54:

AGGCATAGGA CCCGTGTCTT                               20

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 55:

CTTCTTTGGA GAAAG TGG

What is claimed is:

1. A synthetic oligonucleotide useful as an amplifier probe in a sandwich hybridization assay for HTLV-1, wherein said oligonucleotide consists of:
   a first segment having a minimum length of about 25 nucleotides and a maximum length of about 100 nucleotides which segment is at least 90% homologous to a segment of HTLV-1 nucleic acid, wherein said first segment comprises a nucleotide sequence selected from the group consisting of SEQ ID NOS: 6–41; and
   a second segment consisting of a nucleotide sequence which is at least 90% homologous to an oligonucleotide segment of a nucleic acid multimer wherein said second segment is not complementary to HTLV-1 nucleic acid;
   and optionally one or more noncomplementary segments each consisting of a nucleotide sequence that is not complementary to HTLV-1 nucleic acid.

2. The synthetic oligonucleotide of claim 1, wherein said second segment comprises SEQ ID NO:54.

3. The synthetic oligonucleotide of claim 1, wherein said first segment consists of a nucleotide sequence selected from the group consisting of SEQ ID NOS: 6–41.

4. A synthetic oligonucleotide useful as a capture probe in a sandwich hybridization assay for HTLV-1, wherein the synthetic oligonucleotide consists of:
   a first segment having a minimum length of about 25 nucleotides and a maximum length of about 100 nucleotides which segment is at least 90% homologous to a segment of HTLV-1 nucleic acid, wherein said first segment comprises a nucleotide sequence selected from the group consisting of SEQ ID NOS: 42–53; and
   a second segment consisting of a nucleotide sequence which is at least 90% homologous to an oligonucleotide bound to a solid phase wherein said second segment is not complementary to HTLV-1 nucleic acid;
   and optionally one or more noncomplementary segments each consisting of a nucleotide sequence that is not complementary to HTLV-1 nucleic acid.

5. The synthetic oligonucleotide of claim 4, wherein said second segment comprises SEQ ID NO:55.

6. The synthetic oligonucleotide of claim 4, wherein said first segment consists of a nucleotide sequence selected from the group consisting of SEQ ID NOS: 42–53.

7. A set of synthetic oligonucleotides useful as amplifier probes in a sandwich hybridization assay for HTLV-1, comprising at least two different oligonucleotide probes, wherein each oligonucleotide probe consists of:
   a first segment having a minimum length of about 25 nucleotides and a maximum length of about 100 nucleotides which segment is at least 90% homologous to a segment of HTLV-1 nucleic acid, wherein said first segment comprises a nucleotide sequence selected from the group consisting of SEQ ID NOS: 6–41; and
   a second segment consisting of a nucleotide sequence which is at least 90% homologous to an oligonucleotide segment of a nucleic acid multimer wherein said second segment is not complementary to HTLV-1 nucleic acid;
   and optionally one or more noncomplementary segments each consisting of a nucleotide sequence that is not complementary to HTLV-1 nucleic acid.

8. The set of synthetic oligonucleotides of claim 7, wherein each said second segment comprises SEQ ID NO:54.

9. The set of synthetic oligonucleotides of claim 7, wherein said set comprises at least five different oligonucleotide probes.

10. The set of synthetic oligonucleotides of claim 7, wherein each of said first segments consists of a nucleotide sequence selected from the group consisting of SEQ ID NOS: 6–41.

11. A set of synthetic oligonucleotides useful as capture probes in a sandwich hybridization assay for HTLV-1, comprising at least two different oligonucleotide probes, wherein each oligonucleotide probe consists of:
   a first segment having a minimum length of about 25 nucleotides and a maximum length of about 100 nucleotides which segment is at least 90% homologous to a segment of HTLV-1 nucleic acid, wherein said first segment comprises a nucleotide sequence selected from the group consisting of SEQ ID NOS: 42–53; and a second segment consisting of a nucleotide sequence which is at least 90% homologous to an oligonucleotide bound to a solid phase wherein said second segment is not complementary to HTLV-1 nucleic acid;

and optionally one or more noncomplementary segments each consisting of a nucleotide sequence that is not complementary to HTLV-1 nucleic acid.

12. The set of synthetic oligonucleotides of claim 11, wherein each said second segment comprises SEQ ID NO:55.

13. The set of synthetic oligonucleotides of claim 11, wherein said set comprises at least five different oligonucleotide probes.

14. The set of synthetic oligonucleotides of claim 11, wherein each of said first segments consists of a nucleotide sequence selected from the group consisting of SEQ ID NOS: 42–53.

15. A solution sandwich hybridization assay for detecting the presence of HTLV-1 in a sample, comprising (a) contacting the sample with (i) amplifier probes comprising the set of synthetic oligonucleotides of claim 7 and (ii) a set of capture probe oligonucleotides wherein there is a molar excess of amplifier probes and of capture probes over analyte nucleic acid in the sample, wherein said set of capture probe oligonucleotides comprises at least two different oligonucleotides each of which consists of a first segment having a minimum length of about 25 nucleotides and a maximum length of about 100 nucleotides which segment is at least 90% homologous to a segment of HTLV-1 nucleic acid, wherein said first segment comprises a nucleotide sequence selected from the group consisting of SEQ ID NOS: 42–53; and a second segment consisting of a nucleotide sequence which is at least 90% homologous to an oligonucleotide bound to a solid phase wherein said second segment is not complementary to HTLV-1 nucleic acid;

and optionally one or more noncomplementary segments each consisting of a nucleotide sequence that is not complementary to HTLV-1 nucleic acid;

(b) contacting the product of step (a) with said oligonucleotide bound to the solid phase;

(c) thereafter separating materials not bound to the solid phase;

(d) contacting the bound product of step (c) with a nucleic acid multimer, said multimer comprising at least one oligonucleotide segment that is at least 90% homologous to the second segment of the amplifier probe polynucleotide and a multiplicity of second oligonucleotide segments that are at least 90% homologous to a labeled oligonucleotide;

(e) removing unbound multimer;

(f) contacting the solid phase complex product of step (e) with the labeled oligonucleotide;

(g) removing unbound labeled oligonucleotide; and (h) detecting the presence of label in the solid phase complex product of step (g) and, thereby, detecting the presence of virus in the sample.

16. The assay of claim 15, wherein said set of amplifier probes comprises at least five different oligonucleotide probes.

17. The assay of claim 15, wherein said set of capture probes comprises at least five different oligonucleotide probes.

18. A kit for the detection of HTLV-1 in a sample comprising in combination (i) a set of amplifier probe oligonucleotides comprising the set of oligonucleotides of claim 7;

(ii) a set of capture probe oligonucleotides comprising at least two different oligonucleotides each of which consists of a first segment having a minimum length of about 25 nucleotides and a maximum length of about 100 nucleotides which segment is at least 90% homologous to a segment of HTLV-1 nucleic acid, wherein said first segment comprises a nucleotide sequence selected from the group consisting of SEQ ID NOS: 42–53; and a second segment consisting of a nucleotide sequence which is at least 90% homologous to an oligonucleotide bound to a solid phase wherein said second segment is not complementary to HTLV-1 nucleic acid;

and optionally one or more noncomplementary segments each consisting of a nucleotide sequence that is not complementary to HTLV-1 nucleic acid;

(iii) a nucleic acid multimer, said multimer comprising at least one oligonucleotide segment that is at least 90% homologous to the second segment of the amplifier probe polynucleotide and a multiplicity of second oligonucleotide segments that are at least 90% homologous to a labeled oligonucleotide; and (iv) a labeled oligonucleotide.

19. The kit of claim 18, wherein said set of amplifier probes comprises at least five different oligonucleotide probes.

20. The kit of claim 18 wherein said set of capture probes comprises at least five different oligonucleotide probes.

* * * * *